US007030978B2

United States Patent
Guetta et al.

(10) Patent No.: US 7,030,978 B2
(45) Date of Patent: Apr. 18, 2006

(54) SYSTEM AND METHOD FOR INSPECTION OF A SUBSTRATE THAT HAS A REFRACTIVE INDEX

(75) Inventors: Avishay Guetta, Rehovot (IL); Haim Feldman, Nof-Ayalon (IL); Ron Naftali, Shoham (IL); Doron Shoham, Rehovot (IL)

(73) Assignee: Applied Materials, Israel, LTD, Rehovot (IL)

( * ) Notice: Subject to any disclaimer, the term of this patent is extended or adjusted under 35 U.S.C. 154(b) by 297 days.

(21) Appl. No.: 10/423,353

(22) Filed: Apr. 25, 2003

(65) Prior Publication Data
US 2004/0246474 A1 Dec. 9, 2004

(51) Int. Cl.
*G01N 21/00* (2006.01)

(52) U.S. Cl. .................. 356/237.2; 356/237.5

(58) Field of Classification Search .. 356/237.1–237.5, 356/364–369, 445–448
See application file for complete search history.

(56) References Cited

U.S. PATENT DOCUMENTS

| 3,614,232 A | 10/1971 | Mathisen |
| 5,768,017 A | 6/1998 | King et al. |
| 5,859,424 A | 1/1999 | Norton et al. |
| 6,184,984 B1 * | 2/2001 | Lee et al. ............ 356/369 |
| 2003/0137659 A1 | 7/2003 | Milshtein |
| 2004/0016896 A1 | 1/2004 | Almogy |

FOREIGN PATENT DOCUMENTS

| EP | 1 265 063 A1 | 12/2002 |
| WO | WO 00/77500 A1 | 12/2000 |

OTHER PUBLICATIONS

"International Search Report", International Searching Authority, PCT/US 03/36140, (May 3, 2004).

* cited by examiner

*Primary Examiner*—Michael P. Stafira
(74) *Attorney, Agent, or Firm*—Tarek N. Fahmi (57) ABSTRACT

A system and method for inspection of a substrate having a first refractive index, the method including the steps of: (i) defining an apodization scheme in response to a characteristic of the layer; (ii) applying an apodizer to apodize a beam of radiation in response to the apodization scheme; (iii) directing the apodized beam of radiation to impinge on the substrate, whereby a plurality of rays are reflected from the substrate; whereas the apodized beam of radiation propagates through an at least partially transparent medium having a third refractive index and an at least partially transparent layer having a second refractive index and is subsequently reflected from the substrate; whereas the second refractive index differs from the first refractive index and from the third refractive index; and (iv) detecting at least some of the plurality of reflected rays.

55 Claims, 11 Drawing Sheets

SYSTEM AND METHOD FOR INSPECTION OF A SUBSTRATE THAT HAS A REFRACTIVE INDEX

FIELD OF THE INVENTION

The present invention relates generally to methods and systems for automated inspection, and specifically to methods for bright field optical inspection in the presence of a transparent or semitransparent film.

BACKGROUND OF THE INVENTION

Interference involving multiple reflections is known in the art. This phenomenon is described at "Fundamentals of Optics", F. A. Jenkins and H. E. White, 4$^{th}$ edition, 1976, pages 286–314. The interference results from multiple reflections of light between two substrates of a thin layer (or film) of transparent material. In other words, a single beam of radiation that is directed towards a thin layer of transparent material that is followed by an object that has a refractive index different from the film causes multiple beams of radiations to be reflected from the thin layer. If the object is transparent or partially transparent the single beam of radiation may result in additional multiple transmitted beam of radiations. The multiple reflected beams of radiations undergo distinct optical paths and generate interference patterns.

This phenomenon may occur in bright field inspection systems for inspecting various objects such as semiconductor wafers. In many cases a thin layer of dielectric material coats the inspected layer of interest. A typical dielectric layer is made of $SiO_2$, silicon nitride, photo resists and so on. Due to the difficulties of producing a uniform layer across the entire wafer during chip manufacturing process, small thickness changes may exist for different dies. These thickness variations are insignificant for the electrical performance of the IC's but may cause significant reflectivity changes in the course of bright field inspection. When wafer inspection includes a comparison of die-to-die images these reflectivity variations may greatly degrade the comparison outcome.

A typical optical inspection system has an objective lens that focuses a beam of radiation onto an inspected object. The beam of radiation can be viewed as a plurality of light rays that are directed towards the inspected object at multiple incidence angles. Objective lenses that are characterized by high numerical apertures can be viewed as being able to direct light rays from large range of incidence angles towards the inspected object.

The optical paths that the multiple rays of light pass until being detected depend upon the thickness of the dielectric layer and the incidence angle. As the thickness of the dielectric layer may vary in a manner that is usually unknown to the detection system, the detected signal may be responsive to the unknown thickness of the layer. The detected signal can vary substantially as a result of said unknown thickness thus causing detection errors.

A prior art optical inspection system may consist of a light source, a high NA objective lens, a detector and associated electronics and software. The prior art system illuminates an inspected object such as but not limited to a wafer, mask, reticle, and the like. The high NA objective lens is used to illuminate the inspected object as well as to collect the back-reflected light, which is then focused onto a detector.

An illuminated wafer can be viewed as being made of a silicon substrate with a thin layer of a dielectric coating on it, though the effective substrate material may be different at different stages of the manufacturing process. In order to calculate the effect of the wafer on the back reflected beam of radiation, the spherical converging beam of radiation that is emitted from the objective is represented by a sum of plane waves with the same wavelength but propagating in different directions. The reflectivity R as function of incident angle is given by the equations below:

$$R = \frac{R^{\parallel} + R^{\perp}}{2}$$

$$R = \frac{(r_{12}^{\eta})^2 + (r_{23}^{\eta})^2 + 2r_{12}^{\eta}r_{23}^{\eta}\cos 2\beta}{1 + (r_{12}^{\eta})^2(r_{23}^{\eta})^2 + 2r_{12}^{\eta}r_{23}^{\eta}\cos 2\beta}; \eta = \parallel \text{ or } \perp$$

$$r_{j,k}^{\parallel} = \frac{n_j \cos\theta_j - n_k \cos\theta_k}{n_j \cos\theta_j + n_k \cos\theta_k};$$

$$r_{j,k}^{\perp} = \frac{n_k \cos\theta_j - n_j \cos\theta_k}{n_k \cos\theta_j + n_j \cos\theta_k};$$

$$n_k \sin\theta_k = n_j \sin\theta_j; (j, k) = (1, 2) \text{ or } (2, 3)$$

$$\beta = \frac{2\pi}{\lambda_0} n_2 h \cos\theta_2;$$

Where $\theta_k$ is the refracted ray angle within the layer k (k=1,2,3 denoting air, dielectric or substrate, respectively) relative to the substrate normal, h is the dielectric layer thickness, $n_k$ is the respective refractive index of layer k, and $\lambda_0$ is the wavelength of the incident light in air. The intensity at the detector is the sum of intensities of all incident rays.

Figure 1A:
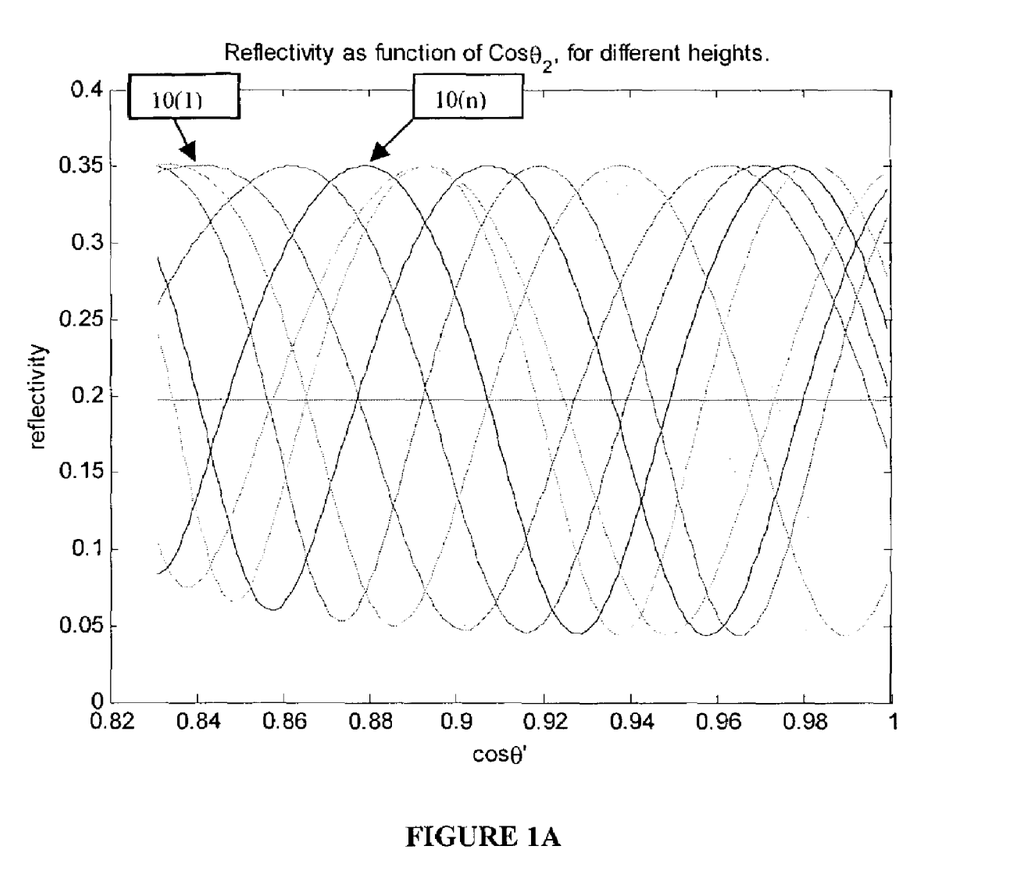
FIG. 1a illustrates the dependence of reflected intensity of a light ray on the angle of incidence and transparent layer thickness.

It is known in the art that the reflected intensities for different rays depend upon the coating layer thickness h, and that this dependence has a periodical behavior, as illustrated by the curves of FIG. 1A. The period is inversely proportional to the thickness h of the thin dielectric layer. Each curve represents the dependence of the reflected intensity of rays on the angle of incidence, for a single thin layer thickness.

SUMMARY OF THE INVENTION

The invention is based on the assumption that the dependence between the thin dielectric layer thickness and the power of a detected light signal may be reduced by preventing some of the light from reaching the thin dielectric layer and/or by preventing some of the reflected light from being detected. The invention provides an overall transfer function that is substantially not sensitive to thickness variation in general or within a range of expected thickness values.

The invention provides a method for optical detection that includes defining an apodization scheme that minimizes detection signal variations in response to dielectric thickness fluctuations and applying this scheme.

It is noted that the apodization scheme may be substantially binary (accordingly, a light portion either passes or not) but may also include partial transmission and even passing the light through multiple apodization filters in order to subtract some light components from the others.

It is noted that this method is useful when performing die to die comparison, and especially when these dies are part of a relatively large wafer, and when the dies are spaced apart from each other, but this is not necessarily so.

The invention provides an apparatus for inspection of a substrate having a first refractive index, whereas the apparatus includes: a radiation source, which is adapted to generate a beam of radiation; an optical objective, which is adapted to direct the beam of radiation to impinge on the substrate, whereby a plurality of rays are reflected from the substrate, whereas the beam of radiation propagates through a medium having a third refractive index and an at least partially transparent layer having a second refractive index and is subsequently reflected from the substrate; whereas the second refractive index differs from the third refractive index and from the first refractive index substrate; whereas at least a some of the reflected rays define a reflected beam of radiation; an apodizer, which is adapted to apodize the reflected beam of radiation in response to an apodization scheme; whereas the apodization scheme is responsive to a characteristic of the layer; and a detector, which is adapted to detect at least one of the reflected rays.

The invention provides an apparatus for inspection of a substrate having a first refractive index, whereas the apparatus includes: a radiation source, which is adapted to generate a beam of radiation; an apodizer, which is adapted to apodize the incident beam of radiation in response to an apodization scheme; whereas the apodization scheme is responsive to a characteristic of the layer; an optical objective, which is adapted to direct the beam of radiation to impinge on the substrate, whereby a plurality of rays are reflected from the substrate, whereas at least a some of the reflected rays define a reflected beam of radiation; whereas the beam of radiation propagates through an at least partially transparent medium having a third refractive index and an at least partially transparent layer having a second refractive index and is subsequently reflected from the substrate; whereas the second refractive index differs from the third refractive index and from the first refractive index; and a detector, which is adapted to detect at least one of the reflected rays.

The invention provides a method for inspection of a substrate having a first refractive index, the method including: providing an inspection system with an apodizer capable of implementing a plurality of apodization schemes; whereas the apodization schemes are responsive to a characteristic of the layer; selecting one of the apodization schemes; applying the apodizer to apodize a beam of radiation in response to the selected apodization scheme; directing the apodized beam of radiation to impinge on the substrate, via an at least partially transparent medium having a third refractive index and an at least partially transparent layer having a second refractive index. The second refractive index differs from the third refractive index and from the first refractive index. The third and first refractive may differ from each other but may also be equal to each other. Whereas a plurality of rays are reflected from the substrate; and detecting at least one of the reflected rays.

The invention provides a method for inspection of a substrate having a first refractive index that is coated by an at least partially transparent layer having a second refractive index, the method including: defining an apodization scheme in response to a characteristic of the layer; directing a beam of radiation to impinge on the substrate; whereas the beam of radiation propagates through an at least partially transparent medium having a third refractive and via the layer and is subsequently reflected from the substrate; whereas the second refractive index differs from the third refractive index and from the first refractive index; applying an apodizer to apodize a reflected beam of radiation being reflected from the substrate, in response to the apodization scheme; and detecting at least a portion of an apodized beam of radiation that passes through the apodizer.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

In the context of the present patent application and in the claims, the choice of incident (and/or reflected) beam shape (and possibly other ancillary characteristics, such as the phase profile across the beam of radiation) and the method of creating the desired shape are referred to as an "apodization scheme." The element used to impose the desired apodization on the incident beam of radiation is referred to herein as an "apodizing filter." In most of the embodiments described hereinbelow, the apodizer filter is positioned at an entrance pupil 30 of the illumination optics and/or at an exit pupil of the collection optics. A beam of radiation is thus apodized by appropriate selection of the shape, dimensions and other characteristics of the apodizing filter.

In the context of the present patent application and in the claims, the presence of a layer at proximity of a substrate whereas a radiation beam passes through the layer before impinging on the substrate is referred to as a layer that coats the substrate or covers the substrate. Usually, the layer coats the substrate, but this is not necessarily so.

FIG. 1A illustrates the dependence of reflected light ray intensity on the angle of incidence and transparent layer thickness. The vertical axis represents the reflectivity ratio while the horizontal axis represents the angle of refraction of a light ray within the layer, and more exactly the cosine of said angle. FIG. 1 illustrates multiple curves, 10(1)–10(h), each representative of the relationship between said angle and intensity for a certain thickness of the transparent layer. Each curve has a period, said period usually being inversely proportional to said thickness.

Figure 1B:
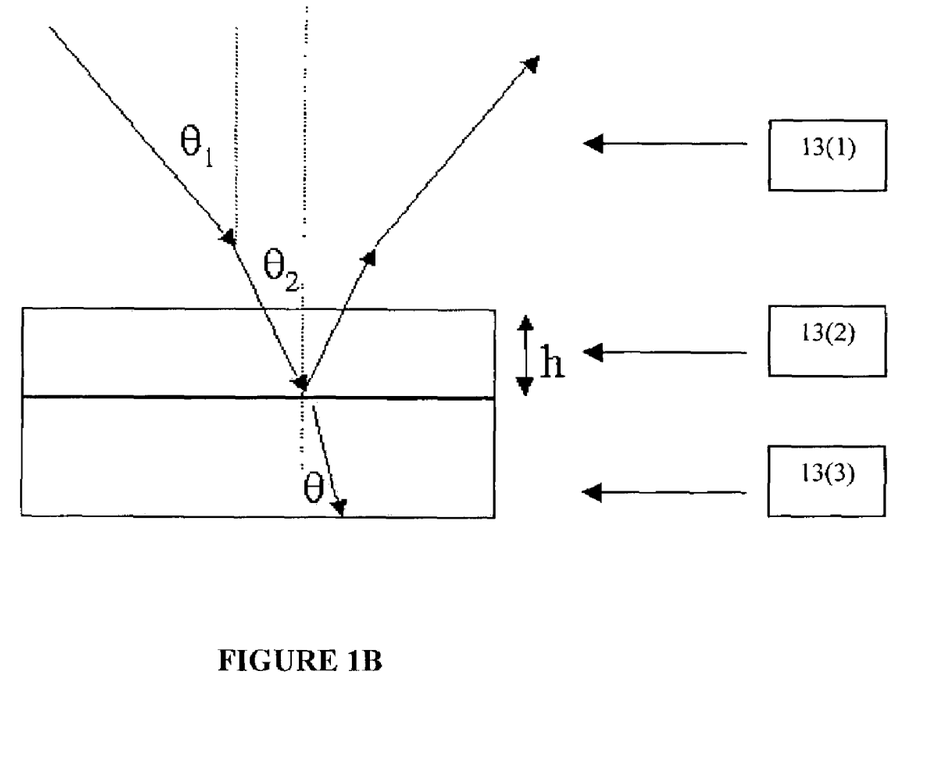
FIG. 1b illustrates the optical path of a light ray that passes through a medium, a layer and is reflected by a substrate.

FIG. 1B illustrates a medium 13(1), layer 13(2) and an inspected substrate 13(3) and a single reflected ray. The difference between the refractive index of said medium, layer and substrate introduce changes in the optical path of the ray.

It is noted that the thickness of the thin dielectric layer, of interest in this invention, may be relatively small in relation to the illuminated light wavelength but may be larger than said wavelength. Typically, the thickness ranges between few (such as five) wavelengths to a portion (one half, one third) of said wavelength.

An inspection system that has a certain collection numerical aperture can be viewed as being able to illuminate and collect reflected light rays over a certain range of incidence angles, each collected light ray associated with a certain point along the horizontal axis of curves 10(1)–10(n), thus the dependence of the intensity of the overall detected signal vs. thickness of the transparent layer may be graphically illustrated by a curve that, at each point, represents the sum of multiple points of a certain curve associated with a certain thickness.

Figure 4:
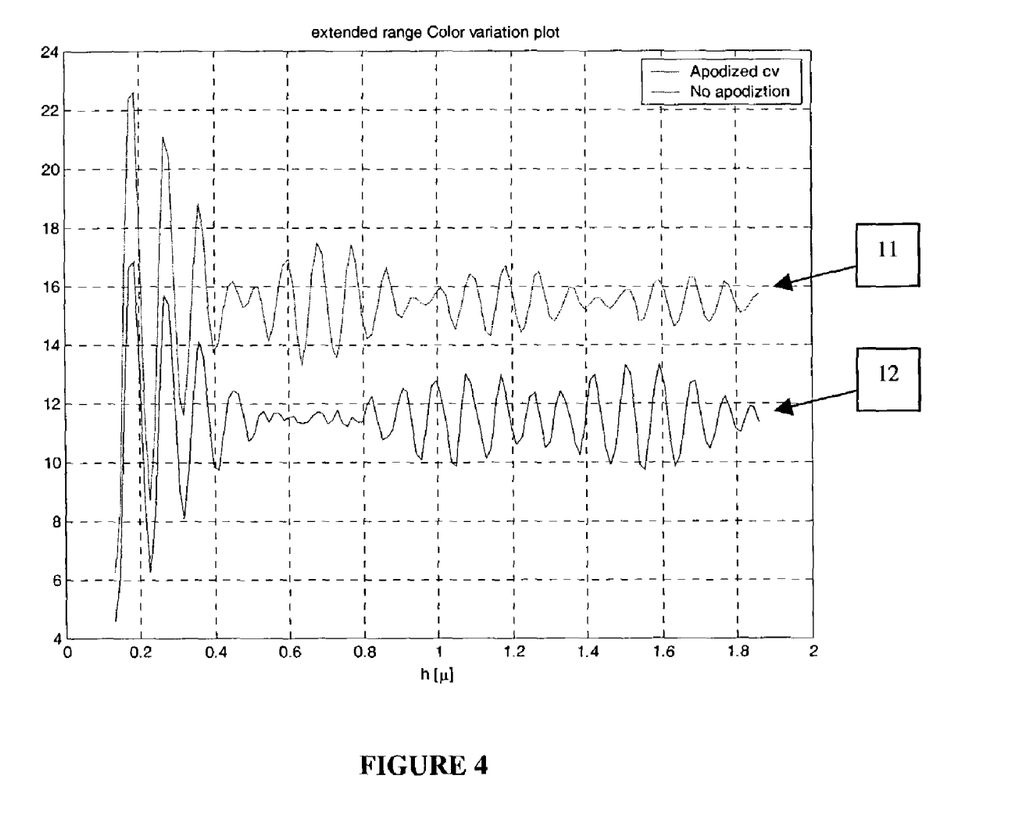
FIG. 4 illustrates the dependence of the intensity of a detected beam of radiation on the thickness of a thin transparent layer with and without the aperture of FIG. 3.

The dependency between the intensity of the detected signal and the thickness of the dielectric layer is illustrated by curves 11 and 12 of FIG. 4. These two curves differ from each other as one illustrates said dependency without an apodization filter while the other curve illustrates said dependency in the presence of an apodizing filter.

Systems for Inspection

Figure 2A:
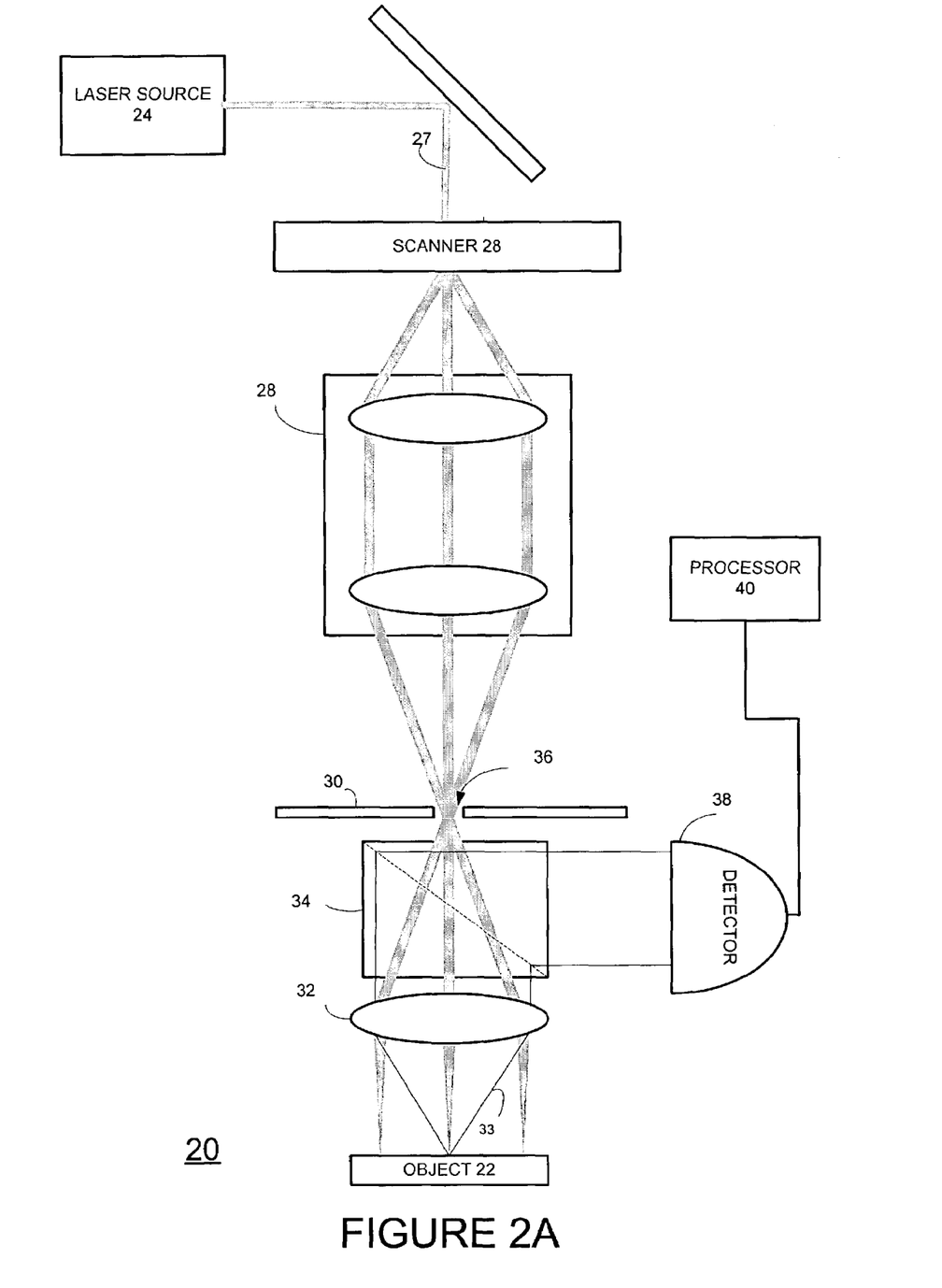
FIGS. 2a–2c are schematic illustrations of an inspection system, in accordance with an embodiment of the present invention.

FIG. 2a is a schematic side view of a system 20 for inspection of a substrate 22, in accordance with an embodiment of the present invention. System 20 is designed for detecting defects in integrated circuit (IC) wafers, and applies apodization techniques, as described hereinbelow, that are particularly useful in the detection of defects that may be smaller than the wavelength of light utilized for inspection. Typically the medium through which the radiation beam propagates is air (usually at a certain vacuum level), but this is not necessarily so and the medium may also include fluids (such as when implementing immersion microscopy).

Therefore, in the description that follows of system 20 and of various apodization schemes that can be used in the system, reference is made to such wafers. It should be understood, however, that these references to IC wafers are made by way of example, and the principles of the present invention may similarly be applied to inspection of substrates of other types. In particular, the principles of system 20 may be applied, mutatis mutandis, to inspection of lithographic masks used in IC production, as well as other substrates, including flat panel displays, such as liquid crystal devices.

System 20 comprises a laser 24 or other source of radiation, conveniently coherent radiation and preferably a narrowband radiation source. The term "narrowband" defines a radiation range that is narrow enough such that the intensity variations versus incidence angle and layer thickness are about the same over the spectral range. The radiation range is narrow enough to prevent color variation cancellation by the broad spectrum of the radiation. A scanner 26, typically an acousto-optic device or rotating mirror, as are known in the art, deflects a laser beam 27 along a scan direction. Relay optics 28 direct the beam of radiation through an apodizer, such as apodizing filter 36 positioned at entrance pupil 30, and a scan objective 32 focuses the beam of radiation onto the substrate of substrate 22. The optical axis of the beam of radiation is normal to the substrate 22. As the objective may have a large NA, multiple rays may be directed at distinct incidence angles towards the substrate 22.

The incident laser light is reflected from the substrate, generating reflected radiation 33, a portion of which is collected by objective 32. A beamsplitter 34 directs the reflected radiation onto a detector. It is noted that the apodizing filter 36 may be located in the illumination path (as illustrated in FIG. 2A) and/or in the collection path of the reflected rays.

According to some aspects of the invention an apodizer is located in the illumination path when the detector is an imaging detector. If the detector is a non-imaging detector, the reflected beam is apodized.

System 20, and especially the apodizing filter 36, are configured to provide a robust transfer function that minimizes the dependence between the thickness of the layer and the detected light level while still allowing at least some of the reflected light rays to reach the detector. A minimum amount of reflected light rays may be defined by signal to noise considerations. An exemplary apodizing filter is described hereinbelow.

A signal processor 40, typically a general-purpose computer with suitable front-end circuits and software, receives the signal output by detector 38. Processor 40 analyzes the signal in order to locate and identify reflective features, such as defects, on the substrate.

Figure 2B:
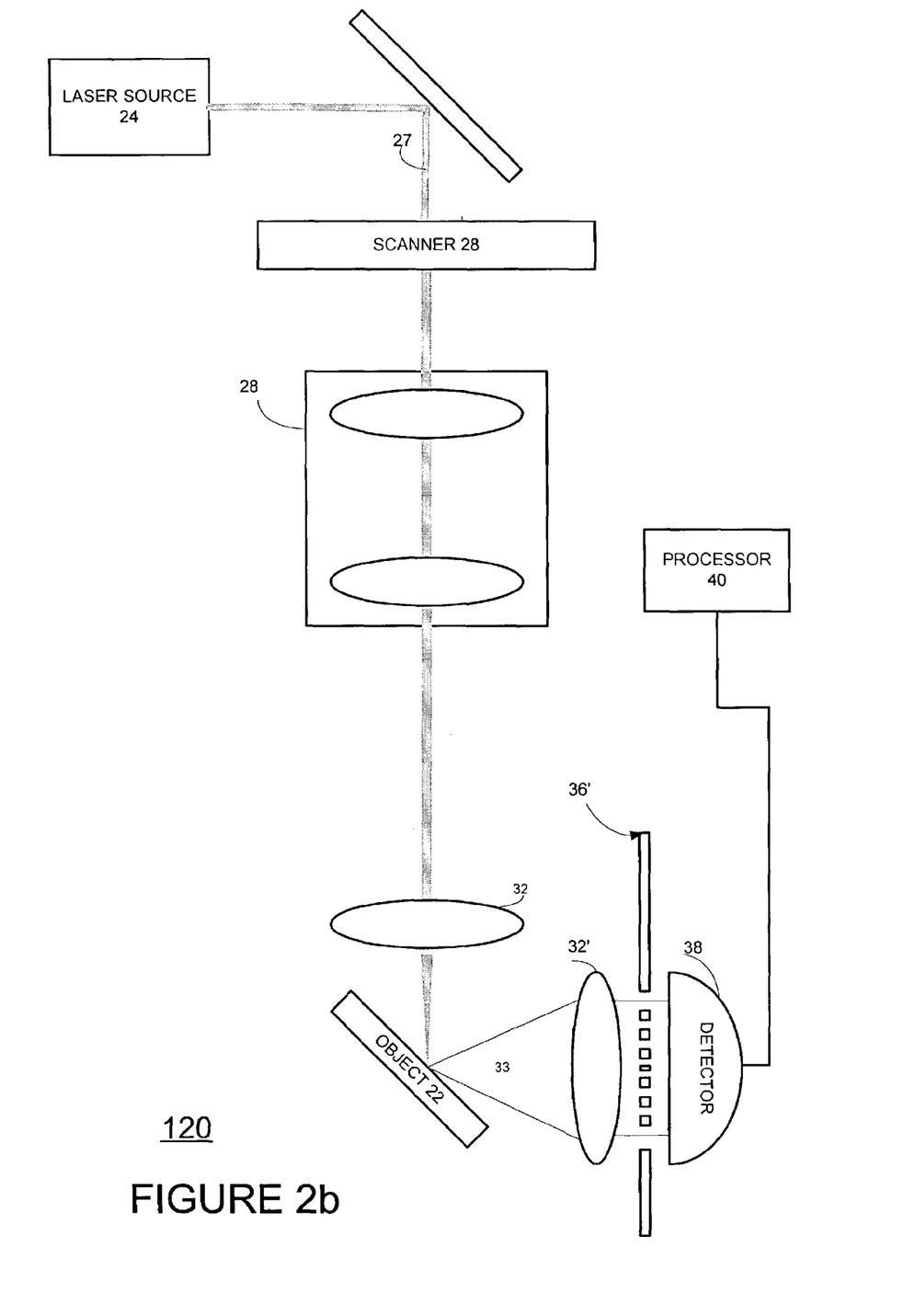

FIG. 2b illustrates system 120. System 120 differs from system 20 by directing a tilted beam of radiation towards substrate (also known in the art as oblique illumination and collection) and by positioning the apodization filter 36' at the collection path (between beam splitter 34 and detector 38).

Figure 2C:
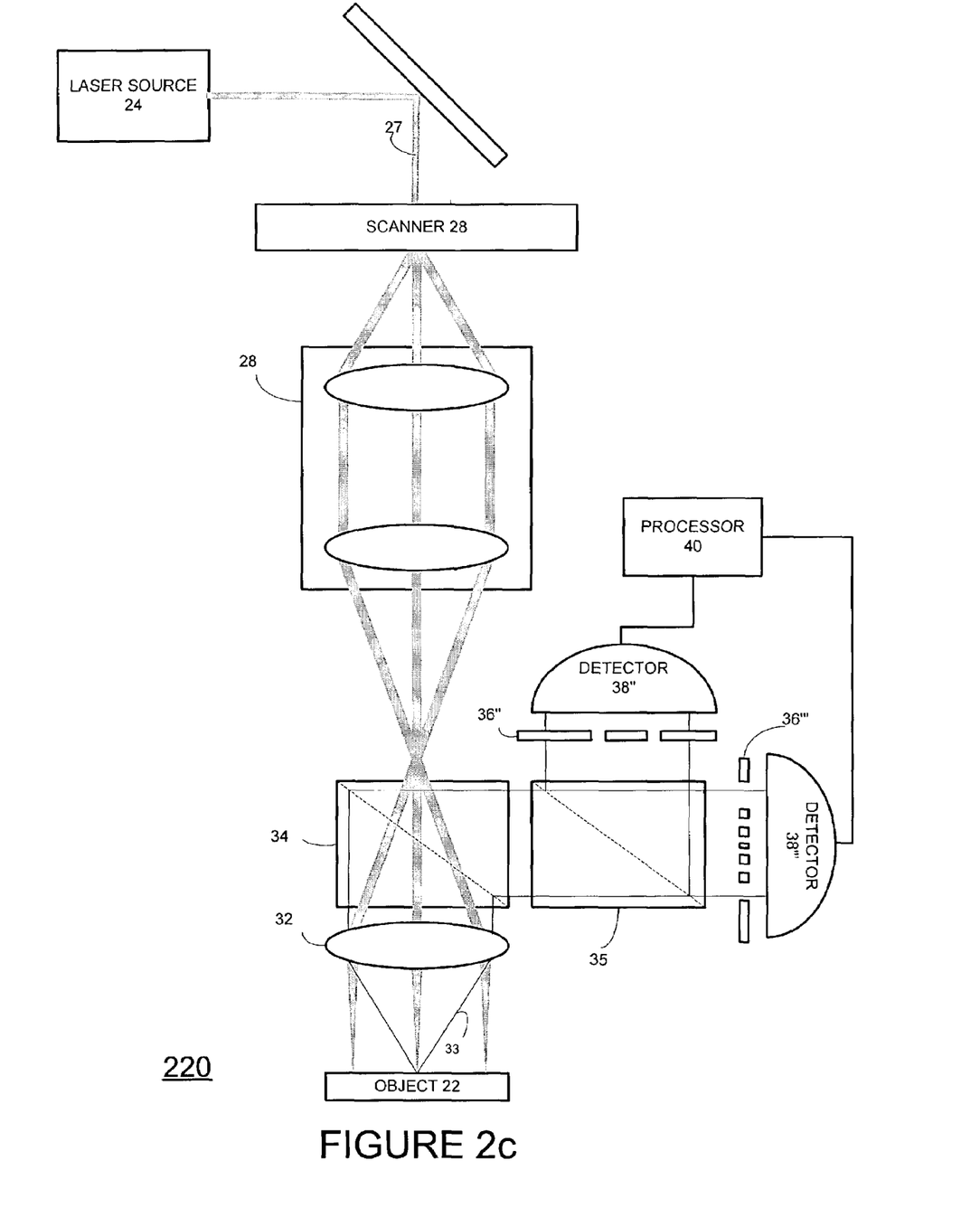

FIG. 2c illustrates system 220. System 220 differs from system 20 by having two apodizing filters 36" and 36''' and two detectors 38' and 38", whereas said apodizing filters are positioned at the collection optics and are located after a secondary beamsplitter 35 that directs reflected light from beamsplitter 34 towards apodizing filters 36" and 36'''. Multiple apodizing filters, detectors and related electronics allow subtraction of detected signals from each other, thus allowing the association of a negative weight to light rays reflected at certain angles.

Apodizing Filter

Figure 3:
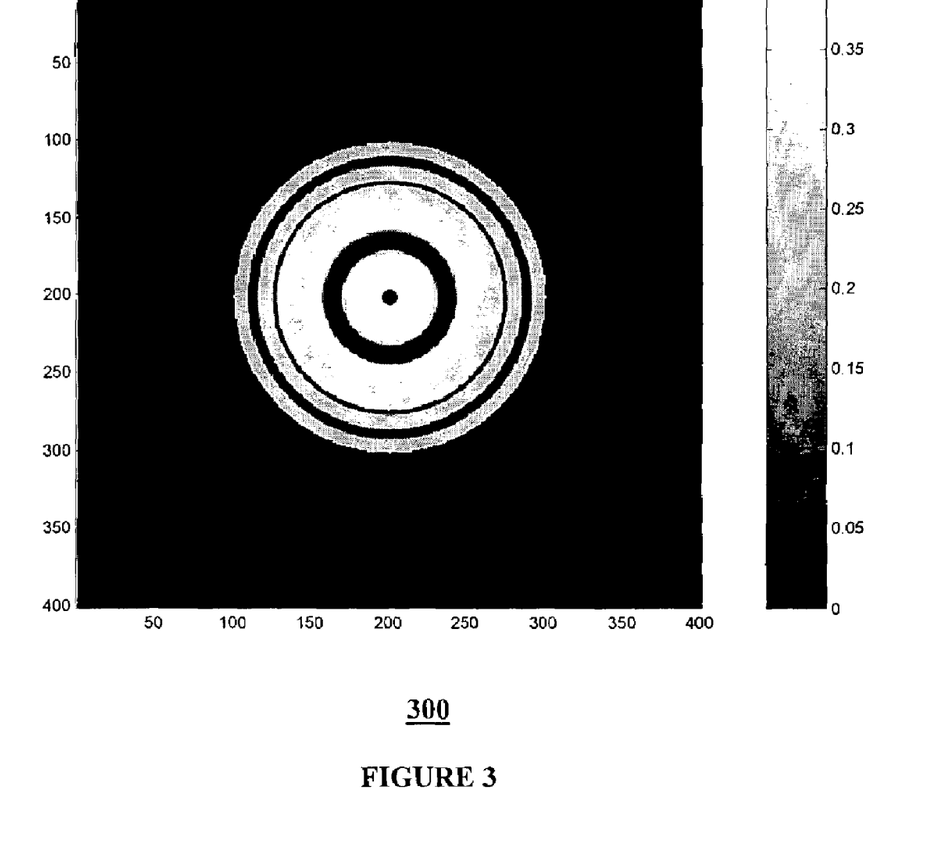
FIG. 3 is a schematic frontal view of an apodizing filter used to apodize a beam of radiation in an inspection system, in accordance with an embodiment of the present invention.

FIG. 3 illustrates an exemplary apodizing filter 300 that includes multiple co-axial opaque and transparent ring shaped regions. Apodizing filter 300 was designed to provide a robust transfer function for a layer that is characterized by a certain transparency value and a thickness within a certain range of thicknesses.

It is noted that the apodizing filter may be designed to provide a robust transform function for other thickness ranges and/or transparency values.

It is further noted that transient regions may be located between at least some of the transparent and opaque regions. An optical density that may decrease from the opaque region towards the transparent region characterizes transient regions.

It is further noted that the various apodizing filters may be defined, each being characterized by a distinct overall transmission factor. The overall transmission factor defines a ratio between the aggregate radiation intensity before being apodized and after the apodization. The overall transmission factor may be responsive to signal to noise considerations.

It is yet noted that the shape of the transient regions may vary, depending upon the application. For example these regions may be shaped as arcs, instead of 360° rings.

It is further noted that at least some of the opaque regions may pass a certain degree of light, said partial transparency reflects a certain weight factor that is given to light that passes through said regions.

It is yet further noted that the apodizing filter may be implemented by a programmable spatial filter, such as an array of controlled micro-shutters that are configured in response to an apodization scheme, micro-mirror arrays, liquid crystals and the like.

According to an aspect of the invention the optical system may include multiple replaceable apodizing filters, such that the apodizing filter that provides the best performance is selected. The replaceable apodizing filters may be arranged within a filter wheel, but other replacement schemes may be applied.

The wheel provides various apodizing filters for use in entrance pupil 30 (or in exit pupil of the collection optics). The wheel may be fabricated using any suitable method known in the art. For example, the wheel may be made from a transparent material, such as glass, with opaque layers, such as chromium, deposited on the glass so as to define the different apertures. The wheel is mounted in system 20 (FIG. 2) at the location of entrance pupil 30 so that the different apodizing filters may be rotated into place.

The selection between the apodizing filters may be in response to predefined parameters of the layer (such as a certain thickness uncertainty range, a certain transparency), but this is not necessarily so, and the replaceable filters may used during a learning period of the system during which the performance of each (or at least some) apodizing filter is measured.

Apodizing Filter Calculation

The following steps calculated the apodizing filter 300 of FIG. 3. It is noted that other method for calculating the apodizing filter may be applied, for example calculations that are based upon other apodization scheme criteria, and the like.

First, a matrix of reflectivity is defined. Said matrix includes multiple samples from the incidence angle and thickness range. The samples are denoted $\theta_i$ and $h_i$ accordingly. The intensity of a detected light signal for a given thickness $h_i$ and for light detected from a range of incidence angles $\theta_j$ is:

$$I(h_i) = \sum_{\cos\theta_j} R\left(h_i, \cos(\theta_j)\right) \equiv \sum_j R_{i,j} = I_i$$

The intensity changes once an apodizing function (T) is introduced:

$$I_i = \sum_j T_j R_{i,j}$$

The apodization may be optimized by various apodization scheme criteria/cost functions. The inventors selected to optimize the variance of $I_i$:

$$\varepsilon \equiv \sum_i (I_i - \bar{I})^2$$

whereas $\bar{I}$ is the average intensity.

The optimization involves defining the following matrix:

$$A = \begin{vmatrix} R_{1,1} & \cdots & R_{M,1} \\ \vdots & & \vdots \\ R_{1,N} & \cdots & R_{M,N} \end{vmatrix} - \begin{vmatrix} \frac{1}{M} & \cdots & \frac{1}{M} \\ \vdots & & \vdots \\ \frac{1}{M} & \cdots & \frac{1}{M} \end{vmatrix} \times \begin{vmatrix} R_{1,1} & \cdots & R_{M,1} \\ \vdots & & \vdots \\ R_{1,N} & \cdots & R_{M,N} \end{vmatrix}$$

Accordingly, the variance may be expressed as:

$$\varepsilon = [T_1 \cdots T_M] \cdot A^T A \cdot \begin{bmatrix} T_1 \\ \vdots \\ T_M \end{bmatrix}$$

It is noted that there is no variance when all the light is blocked (T=0). But as this solution will prevent optical detection there is a need to optimize said variance while a certain amount of light may pass through the apodizing filter, to enable inspection. The amount of light that passes (usually represented as a fraction that defines the overall amount of light that passes through the apodization filter) is represented by a in the following equation:

$$\varepsilon = -\alpha \cdot C^T \cdot T + T^T \cdot A^T A \cdot T$$

Where c is a weighting function it was taken as a vector [1 . . . 1]; and whereas: $0 \leq T_i \leq 1$; i=1 . . . M It is further noted that the apodizing filter of FIG. 3 was calculated under the additional assumptions: the thin dielectric layer is made of $SiO_2$, it is placed above a substrate of Si, the wavelength of the light is 266 nm, the thickness of the thin dielectric layer may vary between 0.5 and 0.7 microns, the apodization weight is 0.1, the numerical aperture of the objective lens is 0.9, the thickness resolution is 4 nm, and the refractive indexes of the substrate and the thin dielectric layers are 3.9+j0.022 and 1.6 respectively.

Inspection Methods

Figure 5A:
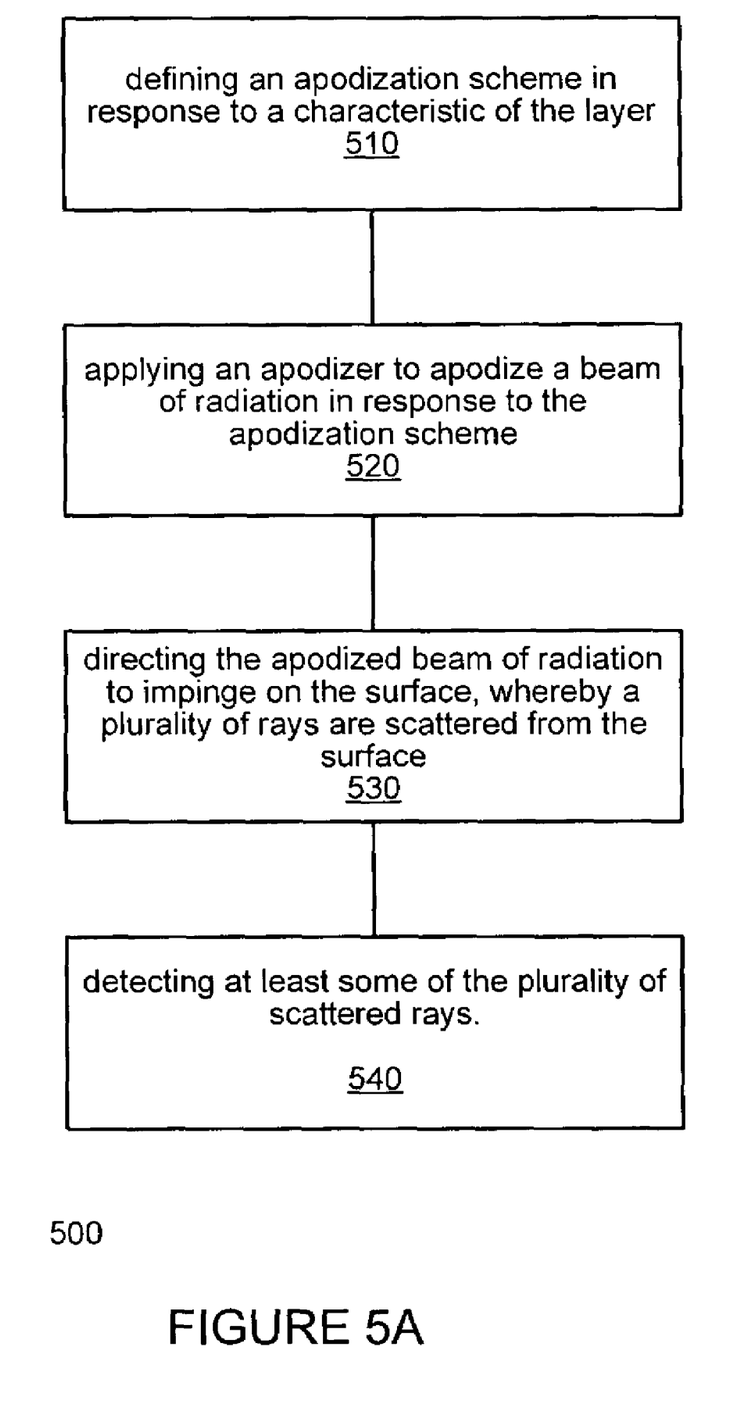
FIGS. 5a–5d are flow charts illustrating methods for inspection, in accordance with various embodiments of the invention.

FIG. 5a illustrates method 500 for inspection of a substrate coated by an at least partially transparent layer. Method 500 starts by step 510 of defining an apodization scheme in response to a characteristic of the layer. The characteristic may be a possible thickness, thickness range or transparency of the layer.

Step 510 may be implemented by the aforementioned equations, but this is not necessarily so. Step 510 may include defining an apodizer overall transparency factor and/or defining an apodization scheme criteria. The apodization scheme criteria may be a variance of reflected ray intensity.

Step 510 may include allocating transparency values to portions of the apodizer. These values may be binary values (zero or one), but this is not necessarily so as they may also be positive values that range between zero and one. It is noted that negative values may be implemented by applying more than a single apodizer, each followed by a detector, and by subtracting detection signals from each other. The apodizer portions may be characterized by a distance between said portion and a center of the apodizer, and are conveniently shaped as co-axial rings.

Step 510 is followed by step 520 of applying an apodizer to apodize a beam of radiation in response to the apodization scheme. Step 520 is followed by step 530 of directing the apodized beam of radiation to impinge on the substrate, whereby pluralities of rays are reflected from the substrate. The apodized beam of radiation propagates through an at least partially transparent medium having a third refractive index, and via the at least partially transparent layer having a second refractive index. The substrate has a first refractive index, whereas the second refractive index differs from the first and third refractive indexes.

Step 530 is followed by step 540 of detecting at least some of the plurality of reflected rays.

According to an aspect of the invention step 510 includes defining multiple apodizers in response to multiple apodization schemes and selecting an apodizer out of the multiple apodizers and applying the selected apodizer.

According to an aspect of the invention step 510 includes setting a characteristic of an entrance pupil, and wherein applying the apodizer comprises passing the beam of radiation through the entrance pupil. Said setting may include placing a programmable spatial filter, such as an array of shutter elements, liquid crystal and the like, in the entrance pupil, and controlling the shutter elements to set a shape of the entrance pupil. On the other hand said setting may include providing a plurality of apodizers, and choosing one of the apodizers to place in the entrance pupil.

Figure 5B:
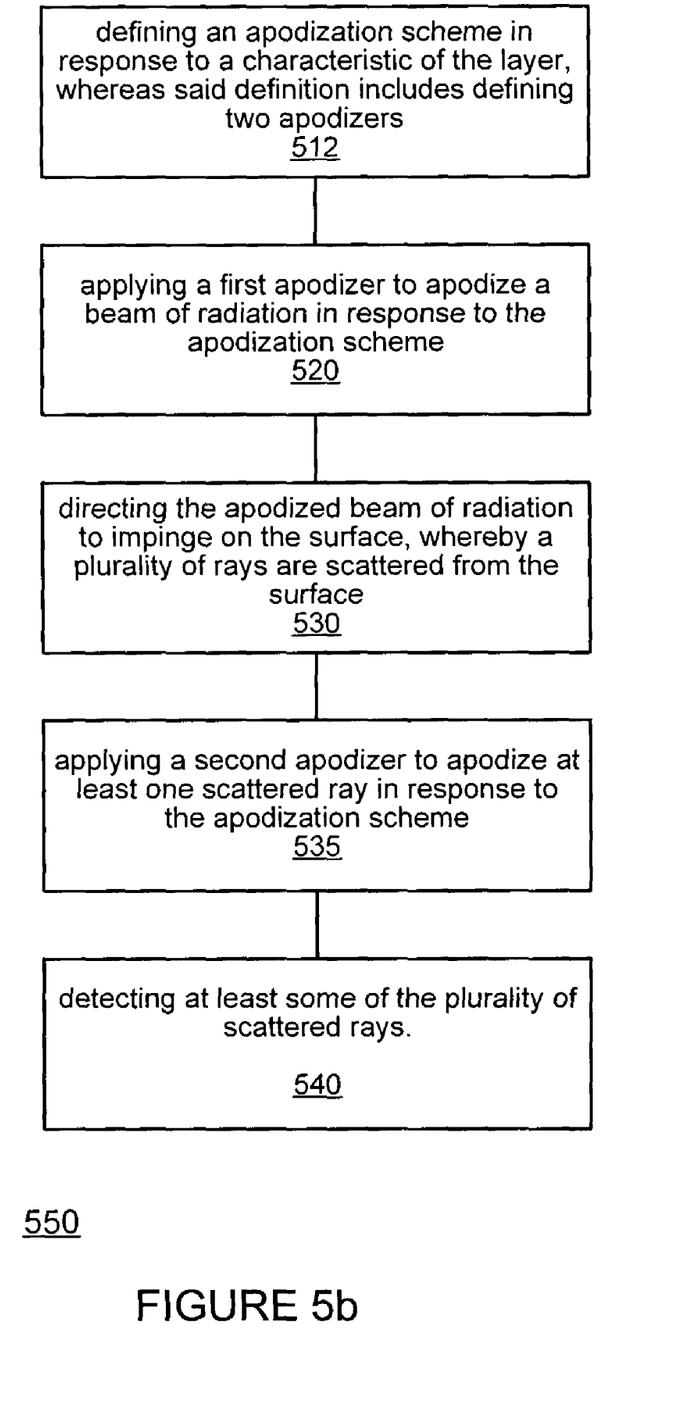

Method 500 includes apodizing a beam of radiation in the illumination path, while the apodizing may also take place in the collection path. Method 550 of FIG. 5b further includes apodization in both the collection and the illumination paths. Accordingly, step 510 of method 500 is replaced by step 512 whereas the apodization scheme includes two apodizers. Method 550 further includes step 535 of applying the second apodizer to apodize at least one reflected ray in response to the apodization scheme.

Figure 5C:
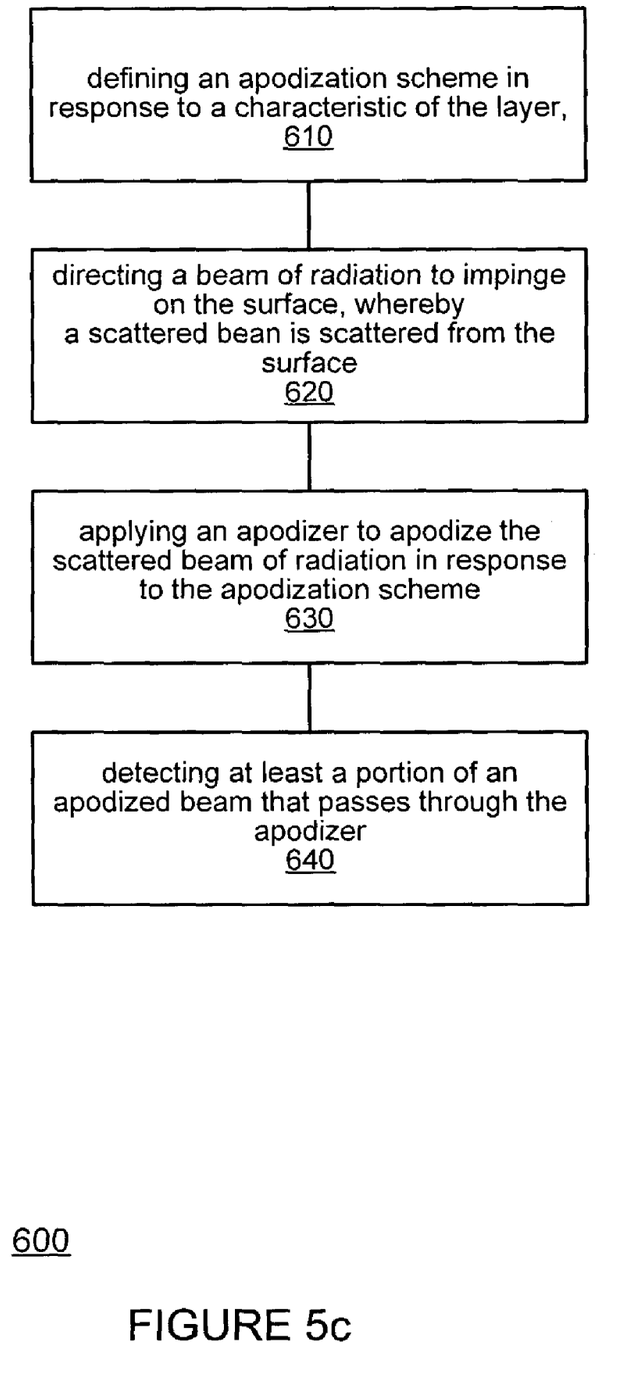

Method 600 of FIG. 5c includes apodization in the collection path, instead of in the illumination path. Method 600 includes step 610 of defining an apodization scheme in response to a characteristic of the layer. It is noted that step 610 is analogous to step 510 but in some cases the definition may be responsive to the position of the apodizer in the collection path instead of the illumination path. Step 610 is followed by step 620 of directing a beam of radiation to impinge on the substrate, whereas a reflected beam is reflected from the substrate. The beam of radiation propagates through an at least partially transparent medium having a third refractive index, and via the at least partially transparent layer having a second refractive index. The substrate has a first refractive index, whereas the second refractive index differs from the first and third refractive indexes.

Step 620 is followed by step 630 of applying an apodizer to apodize a reflected beam of radiation in response to the apodization scheme. Step 630 is followed by step 640 of detecting at least a portion of an apodized beam of radiation that passes through the apodizer.

Figure 5D:
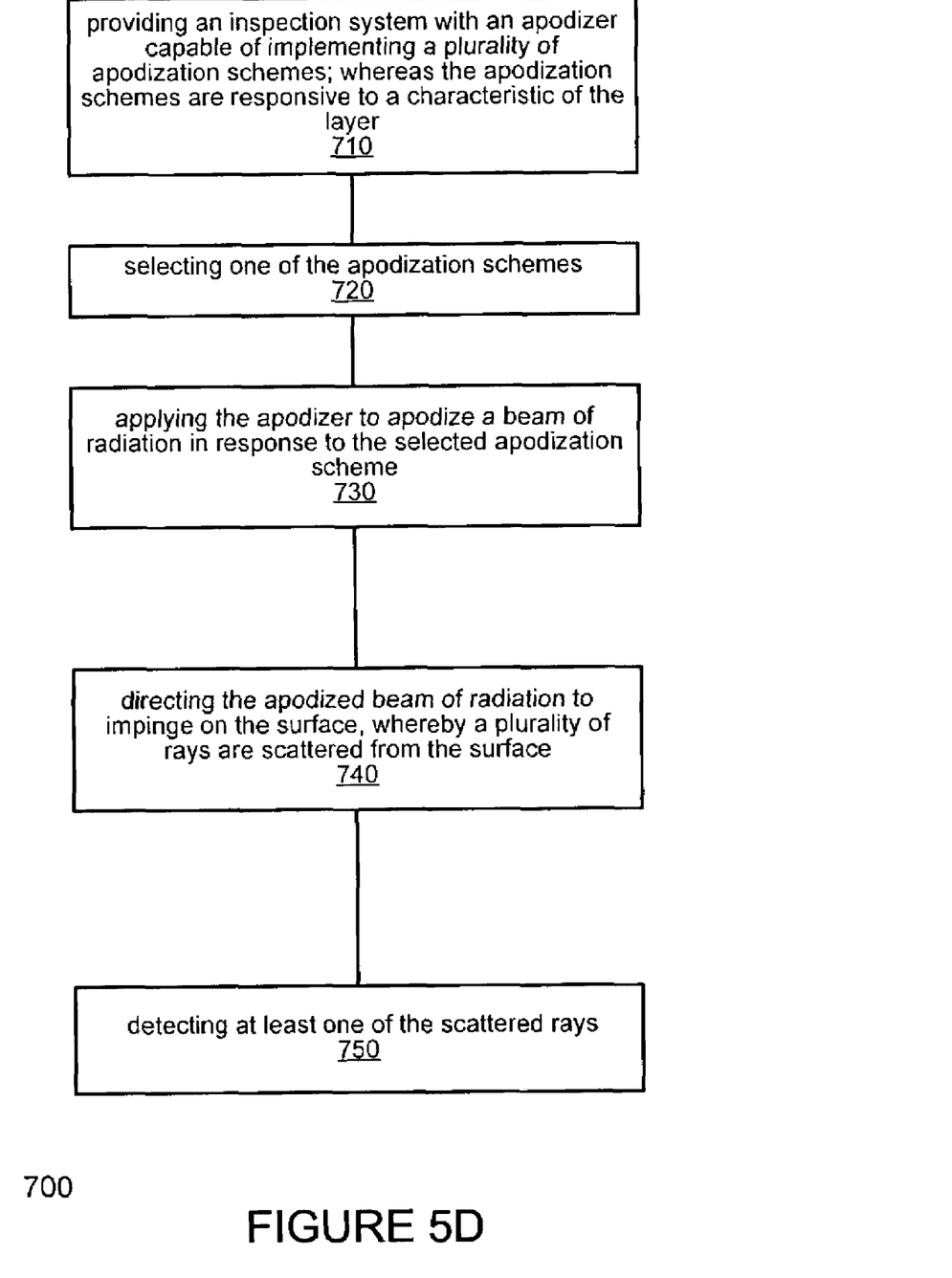

FIG. 5d illustrates a method 700 in which an apodizer out of multiple apodizers is applied. Method 700 starts by step 710 of providing an inspection system with an apodizer capable of implementing a plurality of apodization schemes; whereas the apodization schemes are responsive to a characteristic of the layer. The apodization schemes may be defined in various manners, such as by applying step 510. Step 710 is followed by step 720 of selecting one of the apodization schemes. The selection may be responsive to prior measurements, to a learning period and/or to information relating to the layer. Step 720 is followed by step 730 of applying the apodizer to apodize a beam of radiation in response to the selected apodization scheme. Step 730 is followed by step 740 of directing the apodized beam of radiation to impinge on the substrate, whereby pluralities of rays are reflected from the substrate. The apodized beam of radiation propagates through an at least partially transparent medium having a third refractive index, and via the at least partially transparent layer having a second refractive index. The substrate has a first refractive index, whereas the second refractive index differs from the first and third refractive indexes. Step 740 is followed by step 750 of detecting at least one of the reflected rays.

Although certain apodization schemes are described hereinabove with reference to particular inspection systems 20 and 120, the principles of the present invention may be applied to other types of inspection systems, using such alternative apodization schemes as will be apparent to those skilled in the art. It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

What is claimed is:

1. A method for inspection of a substrate having a first refractive index being covered by an at least partially transparent layer having a second refractive index, the method comprising:

defining an apodization scheme in response to a characteristic of the layer;

applying an apodizer to apodize a beam of radiation in response to the apodization scheme;

directing the apodized beam of radiation, to impinge on the substrate, whereby a plurality of rays are reflected from the substrate; whereas the apodized beam of radiation propagates through an at least partially transparent medium having a third refractive index and the layer having the second refractive index and is subsequently reflected from the substrate; whereas the second refractive index differs from the third refractive index and from the first refractive index; and detecting at least some of the plurality of reflected rays.

2. The method of claim 1, wherein the step of defining comprises defining an apodizer overall transparency factor.

3. The method of claim 1, wherein the step of defining comprising defining an apodization scheme criteria.

4. The method of claim 3, wherein the apodization scheme criteria is a variance of a reflected ray intensity.

5. The method of claim 1, wherein the step of defining comprises allocating transparency values to portions of the apodizer.

6. The method of claim 5, wherein the transparency values are binary.

7. The method of claim 5, wherein the transparency values are positive.

8. The method of claim 5, wherein a portion is characterized by a distance between said portion and a center of the apodizer.

9. The method of claim 5, wherein the portions are shaped as co-axial rings.

10. The method according to claim 1, wherein the step of defining comprises defining multiple apodizers in response to multiple apodization schemes.

11. The method of claim 10, further comprising selecting an apodizer out of the multiple apodizers and applying the selected apodizer.

12. The method of claim 1, wherein the step of defining comprises setting a characteristic of an entrance pupil, and wherein applying the apodizer comprises passing the beam of radiation through the entrance pupil.

13. The method according claim 12, wherein setting the characteristic comprises placing an array of shutter elements in the entrance pupil, and controlling the shutter elements to set a shape of the entrance pupil.

14. The method according to claim 12, wherein setting the characteristic comprises providing a plurality of apodizers, and choosing one of the apodizers to place in the entrance pupil.

15. The method of claim 1, further comprising defining a second apodizer in response to the apodization scheme and applying the second apodizer to apodize at least one reflected ray in response to the selected apodization scheme.

16. The method of claim 1, wherein the characteristic of the layer is at least one possible thickness of the layer.

17. The method of claim 1, wherein the characteristic of the layer is a refractive index of the layer.

18. The method of claim 1, wherein the radiation beam is narrowband.

19. A method for inspection of a substrate having a first refraction index being covered by an at least partially transparent layer having a second refractive index, the method comprising:
defining an apodization scheme in response to a characteristic of the layer;
directing a beam of radiation, to impinge on the substrate; whereas the beam of radiation propagates through an at least partially transparent medium having a first refractive index and the layer having the second refractive index and is subsequently reflected from the substrate; whereas the second refractive index differs from a third refractive index and from the first refractive index;
applying an apodizer to apodize a reflected beam of radiation being reflected from the substrate, in response to the apodization scheme; and
detecting at least a portion of an apodized beam of radiation that passes through the apodizer.

20. The method of claim 19, wherein the step of defining comprises defining an apodization scheme criteria.

21. The method of claim 19, wherein the step of defining comprises allocating transparency values to portions of the apodizer.

22. The method according to claim 19, wherein the step of defining comprises defining multiple apodizers in response to multiple apodization schemes.

23. The method of claim 22, further comprising selecting an apodizer out of the multiple apodizers and applying the selected apodizer.

24. The method of claim 19, wherein the step of defining comprises setting a characteristic of an exit pupil, and wherein applying the apodizer comprises passing the reflected beam of radiation through the exit pupil.

25. The method of claim 19, wherein the characteristic of the layer is at least one possible thickness of the layer.

26. The method of claim 19, wherein the characteristic of the layer is a refractive index of the layer.

27. A method for inspection of a substrate having a first refractive index being covered by an at least partially transparent layer having a second refractive index, the method comprising:
providing an inspection system with an apodizer capable of implementing a plurality of apodization schemes; whereas the apodization schemes are responsive to a characteristic of the layer;
selecting one of the apodization schemes;
applying the apodizer to apodize a beam of radiation in response to the selected apodization scheme;
directing the apodized beam of radiation to impinge on the substrate, whereby a plurality of rays are reflected from the substrate;
directing the apodized beam of radiation, to impinge on the substrate, whereby a plurality of rays are reflected from the substrate; whereas the apodized beam of radiation propagates through an at least partially transparent medium having a first refractive index and the layer having the second refractive index and is subsequently reflected from the substrate; whereas the second refractive index differs from a third refractive index and from the first refractive index; and
detecting at least one of the reflected rays.

28. The method of claim 27, wherein the step of defining comprises defining an apodization scheme criteria.

29. The method of claim 27, wherein the step of defining comprises allocating transparency values to portions of the apodizer.

30. The method of claim 27, wherein the step of defining comprises setting a characteristic of an entrance pupil, and wherein applying the apodizer comprises passing the beam of radiation through the entrance pupil.

31. The method of claim 27, further comprising defining a second apodizer in response to the apodization scheme and applying the second apodizer to apodize at least one reflected ray in response to the selected apodization scheme.

32. The method of claim 27, wherein the characteristic of the layer is at least one possible thickness of the layer.

33. The method of claim 27, wherein the characteristic of the layer is a refractive index of the layer.

34. An apparatus for inspection of a substrate having a first refractive index being covered by an at least partially transparent layer having a second refractive index, the apparatus comprising:
a radiation source, which is adapted to generate a beam of radiation;
an apodizer, which is adapted to apodize the beam of radiation in response to an apodization scheme; whereas the apodization scheme is responsive to a characteristic of the layer;
an optical objective, which is adapted to direct the apodized beam of radiation to impinge on the substrate, whereby a plurality of rays are reflected from the substrate; whereas the apodized beam of radiation propagates through an at least partially transparent medium having a first refractive index and the layer having the second refractive index and is subsequently reflected from the substrate; whereas the second refractive index differs from a third refractive index and from the first refractive index; and
a detector, which is adapted to detect at least one of the reflected rays.

35. The apparatus of claim 34, wherein the apodizer is characterized by an apodizer overall transparency factor.

36. The apparatus of claim 34, wherein the apodizer is defined in response to an apodization scheme criteria.

37. The apparatus of claim 34, wherein the apodizer comprises multiple portions, each portion is characterized by a transparency value.

38. The apparatus of claim 37, wherein the transparency values are binary.

39. The apparatus of claim 37, wherein the transparency values are positive.

40. The apparatus of claim 37, wherein the portions are shaped as co-axial rings.

41. The apparatus according to claim 34, wherein the apodizer comprises an array of controllable shutter elements.

42. The apparatus of claim 34, further comprising a second apodizer that is positioned such as to apodize at least one reflected ray in response to the apodization scheme.

43. The apparatus of claim 34, wherein the characteristic of the layer is at least one possible thickness of the layer.

44. The apparatus of claim 34, wherein the characteristic of the layer is a refractive index of the layer.

45. The apparatus of claim 34, further comprising additional apodizers, each defined according to an apodization scheme, and means for selecting a selected apodizer out of the additional apodizers and the apodizer.

46. An apparatus for inspection of a substrate having a first refractive index, the apparatus comprising:
  a radiation source, which is adapted to generate a beam of radiation;
  an optical objective, which is adapted to direct the beam of radiation to impinge on the substrate, where by a plurality of rays are reflected from the substrate, whereas at least a some of the reflected rays define a reflected beam of radiation; whereas the beam of radiation propagates through an at least partially transparent medium having a first refractive index and an at least partially transparent layer having a second refractive index and is subsequently reflected from the substrate; whereas the second refractive index differs from a third refractive index and from the first refractive index;
  an apodizer, which is adapted to apodize the reflected beam of radiation in response to an apodization scheme; whereas the apodization scheme is responsive to a characteristic of the layer; and
  a detector, which is adapted to detect at least one of the reflected rays.

47. The apparatus of claim 46, wherein the apodizer is characterized by an apodizer overall transparency factor.

48. The apparatus of claim 46, wherein the apodizer is defined in response to an apodization scheme criteria.

49. The apparatus of claim 46, wherein the apodizer comprises multiple portions, each portion is characterized by a transparency value.

50. The apparatus of claim 46, wherein the transparency values are binary.

51. The apparatus of claim 46, wherein the transparency values are positive.

52. The apparatus according to claim 46, wherein the apodizer comprises an array of controllable shutter elements.

53. The apparatus of claim 46, wherein the characteristic of the layer is at least one possible thickness of the layer.

54. The apparatus of claim 46, wherein the characteristic of the layer is a refractive index of the layer.

55. The apparatus of claim 46, whereas the apodizer is capable of implementing a plurality of apodization schemes; whereas the apodization schemes are responsive to a characteristic of the layer.

* * * * *